United States Patent [19]

Saitoh et al.

[11] Patent Number: 5,050,128

[45] **Date of Patent: * Sep. 17, 1991**

[54] ULTRASONIC PROBE HAVING AN ULTRASONIC PROPAGATION MEDIUM

[75] Inventors: Koetsu Saitoh, Tokyo; Masami Kawabuchi, Yokohama; Masakuni Watanabe, Tokyo, all of Japan

[73] Assignee: Matsushita Electric Industrial Co., Ltd., Osaka, Japan

[ * ] Notice: The portion of the term of this patent subsequent to Feb. 20, 2007 has been disclaimed.

[21] Appl. No.: 453,375

[22] Filed: Dec. 27, 1989

Related U.S. Application Data

[63] Continuation of Ser. No. 240,472, Sep. 6, 1988, abandoned, which is a continuation of Ser. No. 31,732, Mar. 30, 1987, abandoned.

[30] Foreign Application Priority Data

Apr. 2, 1986 [JP] Japan .................................. 61-75703
Apr. 17, 1986 [JP] Japan .................................. 61-88542

[51] Int. Cl.[5] .................................. A61B 8/00

[52] U.S. Cl. .................................. 367/7; 367/152; 128/662.03; 310/340

[58] Field of Search .................... 367/7, 11, 150, 152, 367/155; 181/176, 175, 167, 168, 294; 381/88; 364/413.25; 73/642, 644; 128/663.01; 310/328, 334-336, 340

[56] References Cited

U.S. PATENT DOCUMENTS

| | | | |
|---|---|---|---|
| 2,416,324 | 2/1947 | Klein | 367/152 |
| 4,004,266 | 1/1977 | Cook et al. | 367/155 |
| 4,211,948 | 7/1980 | Smith et al. | 367/152 |
| 4,307,457 | 12/1981 | Wills | 367/173 |
| 4,442,715 | 4/1984 | Brisken et al. | 128/660 |
| 4,470,308 | 9/1984 | Hayakawa et al. | 367/150 |
| 4,646,754 | 3/1987 | Seale | 128/774 |
| 4,679,179 | 7/1987 | Lally | 367/162 |
| 4,685,090 | 8/1987 | Krevor | 367/154 |
| 4,901,729 | 2/1990 | Saitoh et al. | 128/662.03 |

FOREIGN PATENT DOCUMENTS

| | | |
|---|---|---|
| 0070139 | 1/1983 | European Pat. Off. . |
| 0130709 | 1/1985 | European Pat. Off. . |
| 2554341 | 5/1985 | France . |
| 56-104650 | 8/1981 | Japan . |
| 1474932 | 5/1977 | United Kingdom . |

OTHER PUBLICATIONS

W. Kleemann: "Einführung In Die Rezeptentwicklung Der Gummiindustrie", 2nd ed., 1966, VEB Deutsche Verlag für Grundstoffindustrie, Leipzig, DD, pp. 380-415.
A. S. Craig: "Concise Encyclopaedic Dictionary of Rubber Technology", 1969, Elsevier Publ. Co., Amsterdam, NL, Various Pages.
Webster's Ninth Collegiate Dictionary, 1983, p. 250.
Condensed Chemical Dictionary, 1979, p. 2.

*Primary Examiner*—Daniel T. Pihulic
*Attorney, Agent, or Firm*—Pollock, Vande Sande & Priddy

[57] ABSTRACT

Disclosed is an ultrasonic probe for use in medical diagnostic systems for examination within a human body. The ultrasonic probe comprises an array of transducer elements for transmission of ultrasonic wave into an examined body and for reception of echo waves returning from the examined body. Further included in the ultrasonic probe is an ultrasonic propagation medium which is provided between the transducer element array and the examined body. The ultrasonic propagation medium is made of a synthetic rubber having an acoustic impedance close to that of the examined body and having a low acoustic attenuation coefficient. Preferably, the synthetic rubber is one of butadiene rubber, butadiene-styrene rubber, ethylene-propylene rubber, and acrylic rubber.

3 Claims, 5 Drawing Sheets

ULTRASONIC PROBE HAVING AN ULTRASONIC PROPAGATION MEDIUM

This application is continuation of application Ser. No. 07/240,472filed Sept. 6, 1988, now abandoned, which is a continuation of application Ser. No. 31,732, filed Mar. 30, 1987, now abandoned.

BACKGROUND OF THE INVENTION

The present invention relates generally to an ultrasonic transducer, and more particularly to an ultrasonic probe having an ultrasonic propagation medium for use in medical ultrasonic diagnostic systems for examination and inspection within an examined body.

Various types of ultrasonic probes for medical diagnostic systems have been developed heretofore with a view to meeting the increasing demands for examination accuracy. Ultrasonic probes generally comprise a linear array of transducer elements for transmission of an ultrasonic wave into an examined body in response to electrical signals from a control circuit and reception of echo waves returning from the examined body. Ultrasonic propagation media provided between the array of transducer elements and the examined body are currently employed for the purpose of allowing the ultrasonic probe to come into plane contact with the examined body concurrently with the increase in scanning angle of the ultrasonic probe. Examples of such an ultrasonic probe including an ultrasonic propagation medium are disclosed in Japanese Patent Provisional Publications Nos. 56-104650 and 58-7231. However, such ultrasonic probes provide problems such as deterioration of the ultrasonic image due to a high degree of ultrasonic wave attenuation in the ultrasonic propagation medium. To avoid the deterioration of the ultrasonic image, it would be necessary to further provide a device for compensating for this problem. The provision of such a device results in a complex and costly ultrasonic diagnostic system.

SUMMARY OF THE INVENTION

It is therefore an object of the present invention to provide an ultrasonic probe which is capable of eliminating the image deterioration problem.

With this object and other features which will become apparent as the description proceeds, an ultrasonic probe according to the present invention comprises an array of transducer elements for transmission of ultrasonic waves into an examined body and for reception of echo waves returning from the examined body; and an ultrasonic propagation medium provided between the transducer element array and the examined body, the ultrasonic propagation medium being made of a synthetic rubber having an acoustic impedance close to that of the examined body and having a low acoustic attenuation coefficient. Preferably, the synthetic rubber is one of butadiene rubber, butadiene-styrene rubber, ethylene-propylene rubber, and acrylic rubber.

In accordance with the present invention, there is further provided an ultrasonic probe comprising first transducer means including an array of transducer elements for transmission of ultrasonic waves into an examined body and for reception of echo waves returning from the examined body; second transducer means including a transducing member for transmission of ultrasonic waves into the examined body and for reception of echo waves returning from the examined body, the second transducer means being disposed such that the ultrasonic transmitting and receiving surface thereof is inclined to make an angle with respect to the ultrasonic transmitting and receiving surface of the transducer element array; and an ultrasonic propagation medium provided in front of at least the second transducer means and having an acoustic impedance close to that of the examined body and having a low acoustic attenuation coefficient, wherein the contact surface of the ultrasonic propagation medium with the examined body and the contact surface of the first transducer means with the examined body are substantially on the same plane. Preferably, the ultrasonic propagation medium is made of one of synthetic rubber, polymethyl pentene, polyethylene, thermoplastic elastomer; and the synthetic rubber is one of butadiene rubber, butadiene-styrene rubber, ethylene-propylene rubber, acrylic rubber and silicon rubber.

BRIEF DESCRIPTION OF THE DRAWINGS

The object and features of the present invention will become more readily apparent from the following detailed description of the preferred embodiments taken in conjunction with the accompanying drawings in which.

DETAILED DESCRIPTION OF THE INVENTION

Prior to describing the embodiments of the present invention, a description of a conventional ultrasonic probe will be made with reference to FIG. 1 for a better understanding of the invention.

Figure 1:
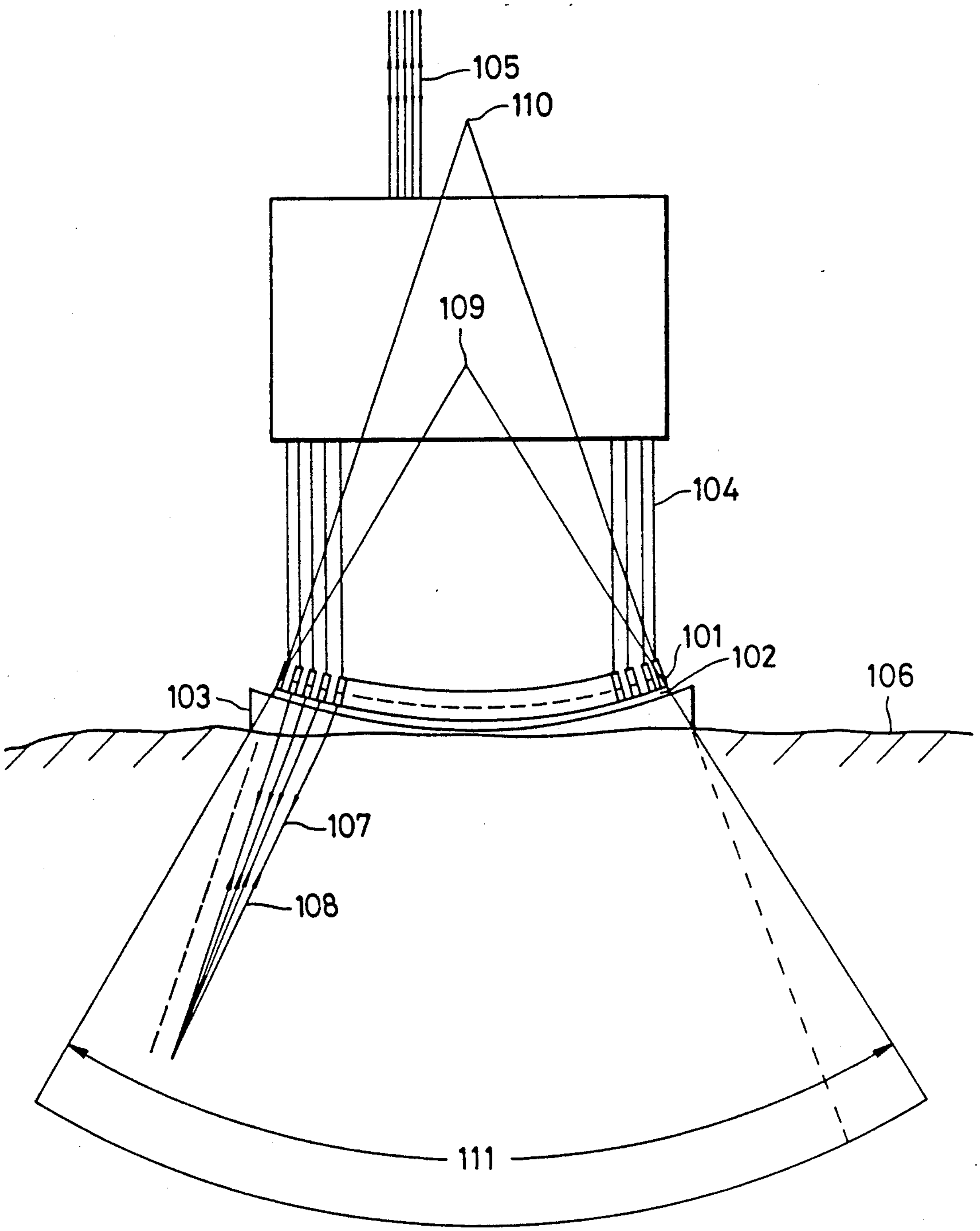
FIG. 1 PRIOR ART
FIG. 1 is an illustration of a conventional ultrasonic probe.

The conventional ultrasonic probe is shown in FIG. 1 as including an array 101 of transducer elements successively arranged in a convex configuration whose center of curvature is illustrated by numeral 110. Also included in the conventional ultrasonic probe are an acoustic matching layer 102 provided along the curved surface of the transducer element array 101 and an ultrasonic propagation medium 103 located in front of the acoustic matching layer 102. The ultrasonic propagation medium 103 has two surfaces, one being concaved to be coincident with the surface of the acoustic matching layer 102 and the other being flat to allow the ultrasonic probe to come into plane contact with a human body 106, i.e., an examined body. The transducer element array 101 transmits ultrasonic waves 107 in response to electrical signals supplied through a cable 105 and lead wires 104 from a control circuit and receives echo waves 108 returning from a region 111 within the examined body 106. The ultrasonic waves 107, 108 are deflected in the ultrasonic propagation medium 103 as they are emitted from a point 109, because the acoustic energy propagates in the ultrasonic propagation medium 103 at a speed lower than in the examined body 106. Thus, the ultrasonic propagation medium 103 serves to increase the scanning angle of the ultrasonic waves and enlarge the examined region. The ultrasonic propagation medium 103 is made of silicon or the like whose acoustic impedance is close to the impedance (about $1.5\times10^5$ g/cm$^2$. s) of the examined body 106 and which has an acoustic property that the acoustic energy propagates at a speed lower than the acoustic velocity (about 1540 m/s) in the examined body 106.

However, the attenuation coefficient of the silicon rubber used for the ultrasonic propagation medium 103 is as great as about 1.5 dB/mm under the condition of a frequency of 3.5 MHz, and there is a considerable difference in thickness between its center portion and its edge portions. This difference causes an extremely great sensitivity difference between the center portion and end portions of the transducer element array 101, resulting in deterioration of an obtained ultrasonic image. A correction circuit would be required additionally to avoid this sensitivity problem.

Figure 2A:
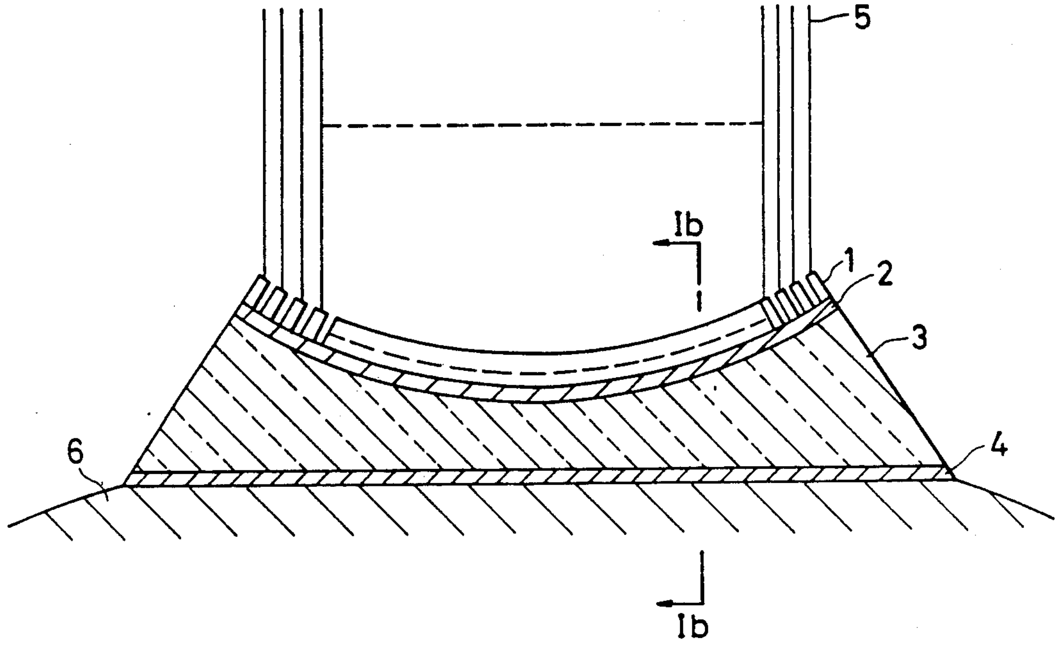
FIGS. 2A and 2B are illustrations of an ultrasonic probe according to an embodiment of the present invention, FIG. 2A being a longitudinal cross-sectional view and FIG. 2B being a cross-sectional view taken along line Ib—Ib of FIG. 2A.
Figure 2B:
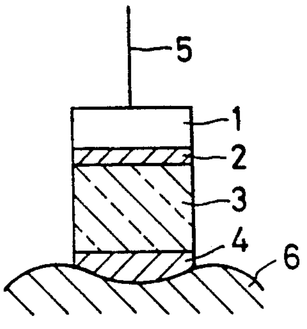

Referring now to FIG. 2A, there is illustrated an ultrasonic probe according to an embodiment of the present invention. FIG. 2B is a cross-sectional view taken along the lines Ib—Ib of FIG. 2A.

In FIGS. 2A and 2B, illustrated at numeral 1 is an array of transducer elements such as piezoelectric elements which are arranged successively in a convexed configuration for emission of diverging beams of acoustic energy into an examined body 6 in response to electrical signals supplied through lead wires 5 from a control circuit, not shown, and for reception of echo waves returning from the inside of the examined body 6. On the front surface of the transducer element array 1 is provided an acoustic impedance matching layer 2 formed in a single layer or multi-layer structure for efficiently transmitting ultrasonic waves. Also included in the ultrasonic probe is an ultrasonic propagation medium 3, one surface of which is concaved so as to agree with the front surface of the acoustic matching layer 2 and the other surface of which is flat to allow the ultrasonic probe to come into plane contact with the examined body 6. The ultrasonic propagation medium 3 is made of synthetic rubber such as butadiene rubber. Further, on the flat surface of the ultrasonic propagation medium 3 is provided an acoustic lens 4 which is of silicon rubber for focusing the emitted ultrasonic beams. Depending on applications, it is also appropriate to provide a backing member on the rear surface of the transducer element array 1.

The operation of the ultrasonic probe is started with the acoustic lens 4 being brought into contact with the examined body 6. The control of transmission of ultrasonic beams is affected by a switching circuit, not shown, such that a group of transducer elements of the array 1 is first driven concurrently in response to signals from a control circuit and the next group of the transducer elements is then driven so as to successively scan the examined body 6. The ultrasonic waves emitted from the transducer element array 1 are transferred through the acoustic matching layer 2, ultrasonic propagation medium 3 and acoustic lens 4 into the examined body 6 and on the other hand the echo waves reflected within the examined body 6 are again respectively received by the same transducer elements after they are passed therethrough. The electrical signals corresponding to the received echo waves are supplied through the lead wires 5 and switching circuit to a diagnostic section and indicated on an indication apparatus as an ultrasonic image.

Figure 3:
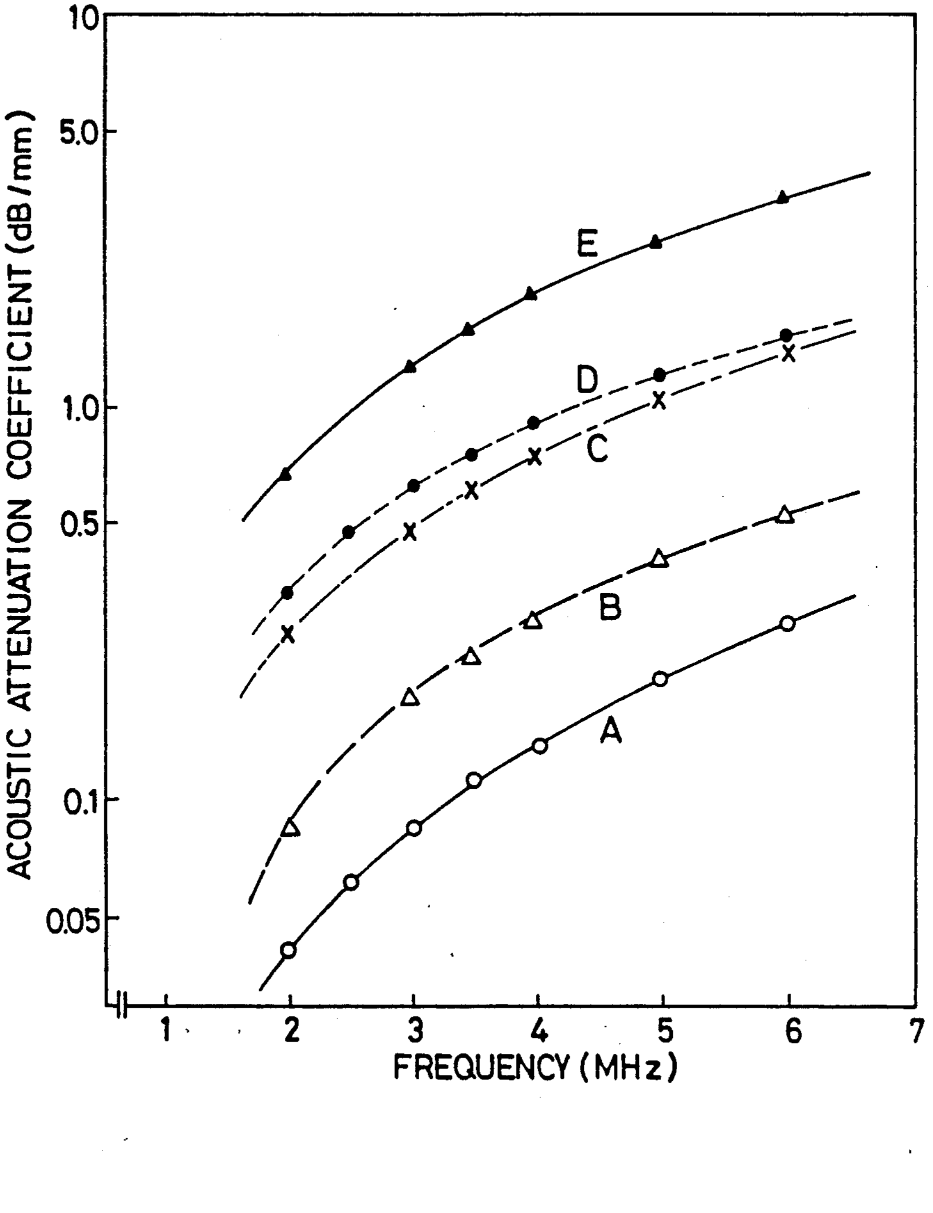
FIG. 3 is a graphic illustration for describing acoustic attenuation coefficients with respect to different materials.

The ultrasonic propagation medium 3 of the ultrasonic probe according to the present invention is basically made of butadiene rubber and further contains, in weight ratio, sulfur of 2 grams, vulcanization accelerator of 1.1 g, zinc oxide of 5 g, and stearic acid of 1 g per butadiene of 100 g. By mixing them to the butadiene, the acoustic impedence becomes $1.49\times10^5$ g/cm$^2$. s which is close to the acoustic impedance, about $1.54\times10^5$ g/cm$^2$. s of a human body, and the acoustic velocity in the ultrasonic propagation medium 3 is 1550 m/sec which is substantially the same acoustic velocity (1540 m/s) as in the human body. Furthermore, the acoustic attenuation coefficients can be obtained as indicated at B in FIG. 3. For example, at a frequency of 3.5 MHz, it is 0.23 dB/mm which is sufficiently lower as compared with the acoustic attenuation coefficient of the conventional silicon rubber-made ultrasonic propagation medium indicated at E in FIG. 3.

Thus, first, since the acoustic impedance of the ultrasonic propagation medium 3 is substantially equal to that of the human body 6, there is no mismatch in the vicinity of the boundary between it and the human body 6, resulting in prevention of resolving power deterioration of images due to multiple reflection. Second, since the acoustic attenuation coefficient is about 1/6.5 of that of the conventional silicon rubber (about 1.5 dB/mm at a frequency of 3.5 MHz), it is possible to sufficiently hold down the dispersion of sensitivity resulting from the difference in thickness between the center portion and end portions of the ultrasonic probe, the thickness difference depending upon the thickness difference between the center portion and end portions of the ultrasonic propagation medium 3. Therefore, a high quality image can be obtained without providing a sensitivity correcting circuit.

Although in the above-described embodiment the ultrasonic propagation medium 3 comprises butadiene rubber, in place of this butadiene rubber, it is also appropriate to use butadiene-styrene rubber, ethylene-propylene rubber, acrylate rubber or the like. Furthermore, although in the above embodiment a description is made in terms of mixing sulfur, vulcanization accelerator, zinc oxide, and stearic acid to the butadiene rubber, it is also appropriate as indicated by A in FIG. 3 to add only vulcanizing agent thereto. It is also appropriate as indicated by C to add carbon, and it is appropriate as indicated by D to add magnesium carbonate. In addition, it is possible to add calcium carbonate, titanium oxide, magnesium oxide and so on. The following table shows acoustic impedances and acoustic velocities with respect to the respective materials.

| Material (FIG. 3) | Acoustic Impedance ($\times$ $10^5$ g/cm$^2$ · sec) | Acoustic Velocity (m/sec) |
|---|---|---|
| A | 1.42 | 1560 |
| B | 1.49 | 1550 |
| C | 1.76 | 1570 |

-continued

| Material (FIG. 3) | Acoustic Impedance ($\times 10^5$ g/cm$^2$ · sec) | Acoustic Velocity (m/sec) |
|---|---|---|
| D | 1.7 | 1550 |

Figure 4:
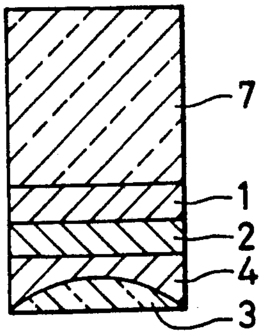
FIG. 4 is a cross-sectional view showing an ultrasonic probe according to another embodiment of the present invention.
Figure 5:
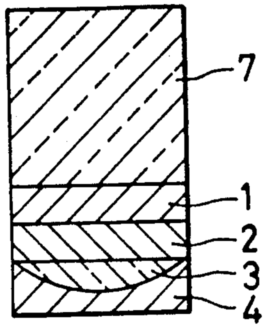
FIG. 5 is a cross-sectional view showing an ultrasonic probe according to a further embodiment of this invention.

FIGS. 4 and 5 show modified embodiments of the present invention in which parts corresponding in function to those in FIG. 2 are designated by the same numerals.

The ultrasonic probe of FIG. 4 comprises an ultrasonic transducer 1 for transmission and reception of ultrasonic waves and an acoustic matching layer 2 provided on the front surface of the ultrasonic transducer 1. As required, the acoustic matching layer 2 is formed in a single layer structure or a laminated structure. On the front surface of the acoustic matching layer 2 is provided an acoustic lens 4 made of polymethyl pentene (TPX), polystyrene or the like having a low acoustic attenuation coefficient and a property that the acoustic velocity therein is higher than in a human body. The front surface of the acoustic lens 4 is concaved and on the concaved surfaced is provided an ultrasonic propagation medium 3 having a corresponding surface and made of a synthetic rubber, for example, butadiene rubber. The other surface, i.e., front surface, thereof is flat for the purpose of allowing the ultrasonic probe to come into plane contact with the human body. Further included in the ultrasonic probe is a backing member 7 which is positioned on the rear surface of the ultrasonic transducer 1.

Since in this embodiment the acoustic lens 4 is positioned between the acoustic matching layer 2 and the ultrasonic propagation medium 3 to allow the ultrasonic propagation medium 3 to directly come into contact with the human body, it is possible to freely determine the configuration of the contact surface with the human body so as to ensure precise contact between the ultrasonic probe and the human body, resulting in improvement of operability. The ultrasonic propagation medium will be made of the same material as in the first embodiment of FIG. 2.

The ultrasonic probe of FIG. 5 also comprises an ultrasonic transducer 1 for transmission and reception of ultrasonic waves and an acoustic matching layer 2 provided on the front surface of the ultrasonic transducer 1. As required, the acoustic matching layer 2 is formed in a single layer structure or a laminated structure. On the front surface of the acoustic matching layer 2 is provided an ultrasonic propagation medium 3 having a surface convexed in the ultrasonic wave transmission direction and further on the convexed surface of the ultrasonic propagation medium 3 is provided an acoustic lens 4 having a concaved surface fitted with the convexed surface of the ultrasonic propagation medium 3 and a flat surface coming into contact with an examined body. The acoustic lens 4 is made of poly methyl pentene (TPX), polystyrene or the like. Also included in the ultrasonic probe is a backing member which is provided on the rear surface of the ultrasonic transducer 1. In the arrangement shown in FIG. 5, for focusing the ultrasonic waves, it is required that the acoustic velocity in the acoustic lens 4 is higher than in the ultrasonic propagation medium 3.

Since in this embodiment a synthetic rubber with an extremely low acoustic attenuation property is employed for the ultrasonic propagation medium 3 unlike polyurethane in conventional probes, it is possible to obtain a high quality image without characteristic deterioration.

The ultrasonic probes of FIGS. 4 and 5 are mainly employed when the frequency is high, and a plastic material with low acoustic attenuation characteristic is used for the acoustic lens 4 in order to hold down the characteristic deterioration due to the acoustic attenuation in the acoustic lens 4. Thus, it is greatly effective to use, for the ultrasonic propagation medium 3, a material with an extremely low attenuation and with an acoustic impedance close to that of the examined body. In the above-mentioned first to third embodiments, it is not always required to fix the ultrasonic propagation medium 3 to others with adhesion.

A further embodiment of the present invention will be described hereinbelow with reference to FIG. 6.

Figure 6:
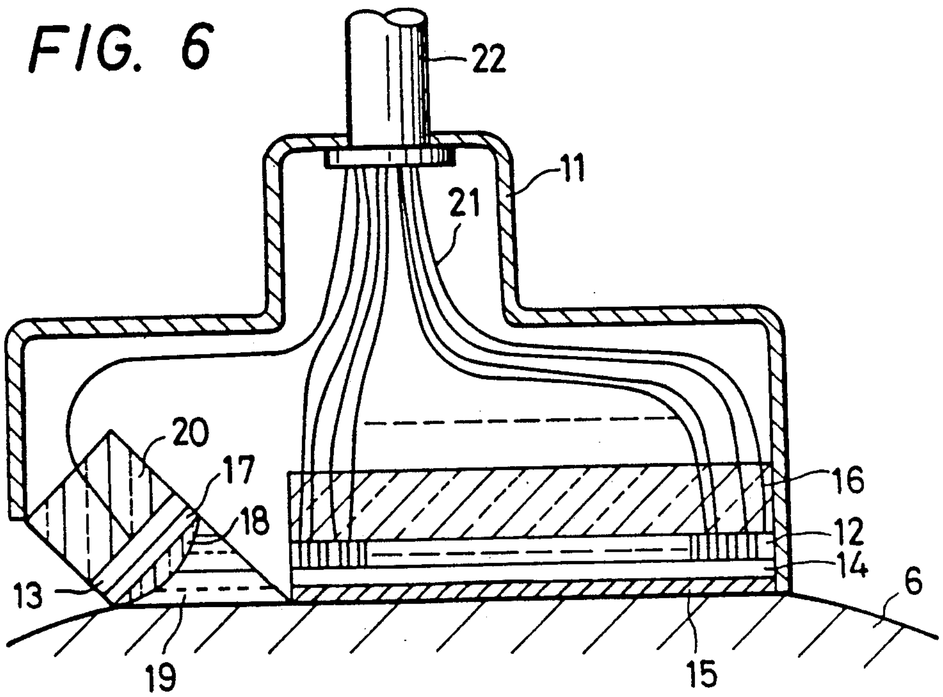
FIG. 6 is a cross-sectional view showing an ultrasonic probe according to the fourth embodiment of this invention.

The probe of FIG. 6 includes a transducer array 12 for obtaining an ultrasonic image within an examined body and a transducer 13 for obtaining an ultrasonic Doppler signal depending upon a blood flow in connection with the ultrasonic image obtained by the transducer array 12. The transducer array 12 has a number of transducer elements linearly and successively arranged. On the front surface of the transducer array 12 is provided an acoustic matching layer 14 and further on the front surface of the acoustic matching layer 14 is provided an acoustic lens 15 made of silicon rubber or the like for focusing ultrasonic waves. A backing member 16 is provided on the rear surface of the transducer array 12. On the other hand, the transducer 13 comprises a single or multiple plate-like elements and is disposed such that the ultrasonic transmitting and receiving surface thereof is inclined to make an acute angle, for example 45-degrees, with respect to the ultrasonic transmitting and receiving surface of the transducer array 12. On the front surface of the transducer 13 is provided an acoustic matching layer 17 and further on the front surface of the acoustic matching layer 17 is provided an acoustic lens 18 made of silicon rubber or the like. On the front surface of the acoustic lens 18 coming into contact with a human body 6 is provided a solid ultrasonic propagation medium 19 with an acoustic impedance close to that of the human body 6 and with a low acoustic attenuation coefficient. The ultrasonic propagation medium 19 has a substantially triangular configuration so that the front surface thereof is on the plane on which the front surface of the acoustic lens 15 is placed. Another backing member 20 is provided on the rear surface of the transducer 13.

The ultrasonic propagation medium 19 comprises one of synthetic rubbers such as butadiene rubber, butadiene-styrene rubber, ethylene-propylene rubber, and acrylic rubber or comprises one of plastic materials such as polymethyl pentene and polyethylene or comprises a thermoplastic elastomer. If using the butadiene, it is possible to add sulfur, vulcanization accelerator, zinc sulfide, and stearic acid, or add any one of the following: vulcanizing agent, carbon, calcium carbonate, titanium oxide, magnesium oxide, magnesium carbonate. The transducer array 12 and transducer 13 are encased in a case 11 and are coupled through lead wires 21 and a cable 22 to an ultrasonic diagnostic apparatus, not shown.

Although in use of the probe of FIG. 6 the acoustic lens 15 and the ultrasonic propagation medium 19 are brought into contact with the examined body 6, the contact surfaces thereof with the examined body 6 are on the same plane and therefore the handling is easy without causing pain to the examined person. Thereafter, the transducer array 12 and the transducer 13 transmit ultrasonic waves into the examined body 6 in response to pulse signals supplied through the cable 22 and the lead wires 21 from the ultrasonic diagnostic apparatus. The transducer array is controlled such that a group of the transducer elements is first concurrently driven and then switched to the next group to perform a scanning. The ultrasonic waves transmitted from the transducer array 12 are transferred through the acoustic matching layer 14 and the acoustic lens 15 into the examined body 6, and the echo waves reflected in the examined body 6 are received by the ultrasonic array 12 after being passed through the acoustic lens 15 and the acoustic matching layer 14. In response to the reception, the transducer array 12 generates corresponding signals which are in turn supplied through the lead wires 21 and cable 22 to the diagnostic apparatus and indicated as a diagnostic image in an indicator device.

On the other hand, the ultrasonic waves emitted from another transducer 13 are transferred through the acoustic matching layer 17, acoustic lens 18 and ultrasonic propagation medium 19 into the examined body 6. The echo waves reflected therewithin are received by the transducer 13 after being passed through the ultrasonic propagation medium 19, acoustic lens 18 and acoustic matching layer 17 and corresponding signals are then supplied through the lead wires 21 and the cable 22 to the diagnostic apparatus to extract an ultrasonic Doppler signal depending on blood flow. Since the ultrasonic propagation medium 19 has an acoustic impedance close to that of the examined body 6 and has a low ultrasonic attenuation coefficient as described above, the Doppler signal can be extracted with precision. In addition, the medium 19 is not lost because it is a solid, thereby permitting certain extraction.

Although in the embodiment of FIG. 6 the ultrasonic propagation medium 19 is arranged to come into contact with the examined body 6, it is also appropriate such that the acoustic lens 18 is provided on the front surface of the ultrasonic propagation medium 19 and comes into contact with the examined body 6. It is allowed to be arranged such that the transducer array 12 and the transducer 13 are attached to each other.

Figure 7:
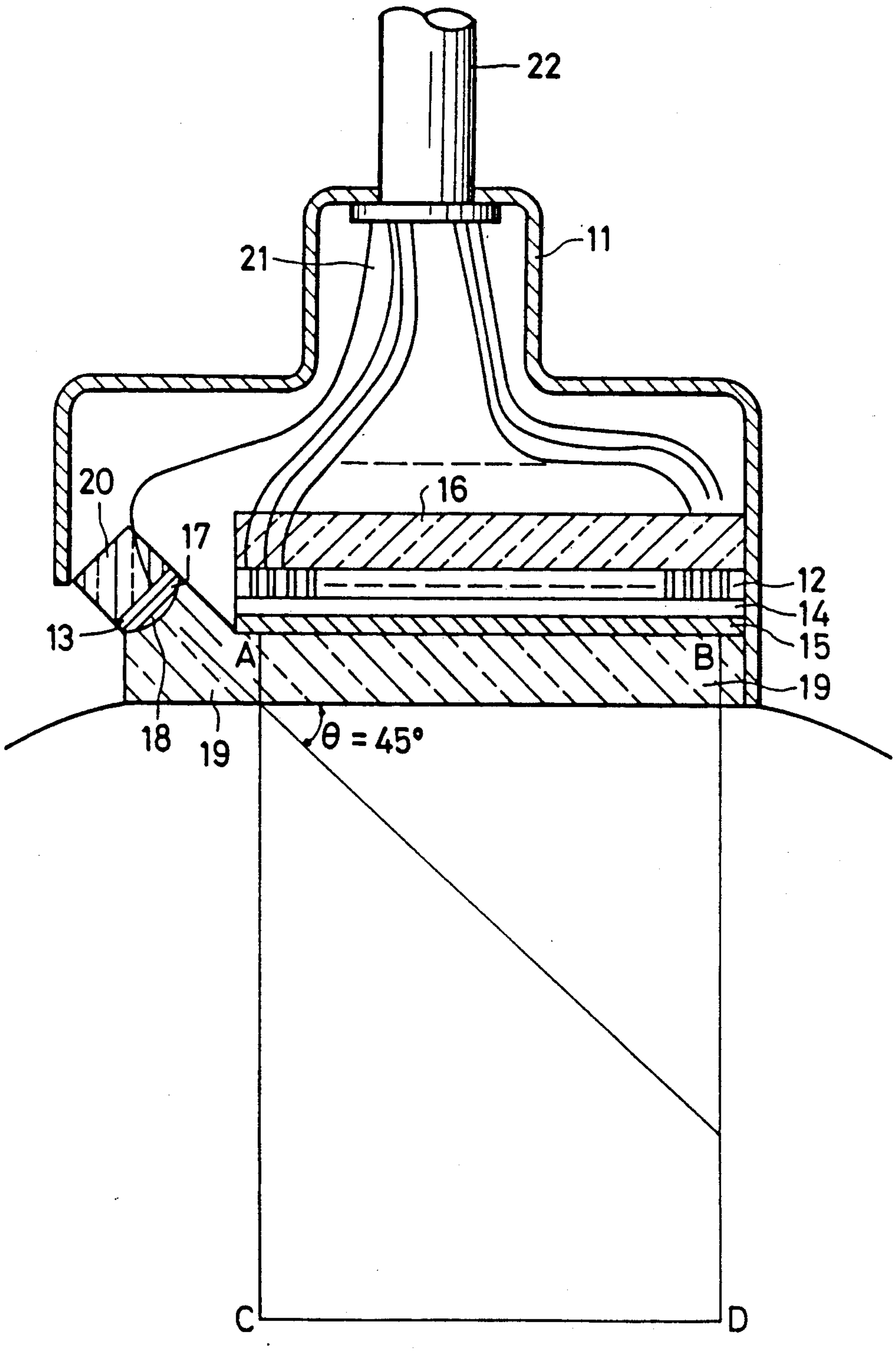
FIG. 7 is a cross-sectional view illustrating an ultrasonic probe according to the fifth embodiment of this invention.

FIG. 7 shows a modified embodiment of the present invention in which parts corresponding in function to those in FIG. 6 are designated by the same numerals and the description thereof are omitted for brevity.

One difference between the probes of FIGS. 6 and 7 is that an ultrasonic propagation medium 19 is positioned in association with both a transducer array 12 and a transducer 13, that is, the medium 19 is placed in front of the transducer array 12 and the transducer 13.

The transducer 13 is disposed such that the ultrasonic transmitting and receiving surface is inclined to make an acute angle, for example 45-degrees, with respect to the ultrasonic transmitting and receiving surface of the transducer array 12. The ultrasonic propagation medium 19 is made of butadiene rubber or the like having an acoustic impedance close to that of an examined human body 6 and having a low acoustic attenuation coefficient.

On the other hand, an ultrasonic image obtained by the transducer array 12 covers the range indicated by characters A, B, C, D in FIG. 7, including the ultrasonic propagation medium 19. This substantially eliminates the problems that a portion of the image corresponding to the body portion near the probe becomes unclear because of acoustic mismatch and because noises are introduced up to about 10 mm depth. Thus, it is possible to obtain a distinct image of blood vessels in the vicinity of the surface of the examined body and to extract the ultrasonic Doppler signal with an excellent S/N ratio.

Although in the embodiment of FIG. 7 the ultrasonic propagation medium 19 is arranged to come into contact with the examined body 6, it is also appropriate to be arranged such that the acoustic lens 15 is provided on the front surface of the ultrasonic propagation medium 19 to come into contact with the examined body. Furthermore, although in the embodiments of FIGS. 6 and 7 the end surfaces of the transducer array 12 side section and the transducer 13 side section are arranged to be on the same plane, it is also appropriate that it is arranged such that they are not on the same plane. However, if they are on the same plane, the contact of the probe with the examined body becomes excellent and the operation thereof becomes easy.

It should be understood that the foregoing relates to only preferred embodiments of the present invention, and that it is intended to cover all changes and modifications of the embodiments of this invention herein used for the purpose of the disclosure, which do not constitute departures from the spirit and scope of the invention.

What is claimed is:

1. An ultrasonic probe comprising:

ultrasonic transducer means for transmission of ultrasonic waves into a water or living body and for reception of echo waves returning from said water or living body; and an ultrasonic propagation medium provided directly or indirectly between said ultrasonic transducer means and said water or living body, said ultrasonic propagation medium being made of butadiene rubber, butadiene rubber which contains sulfur, vulcanization accelerator, zinc oxide and stearic acid or butadiene rubber which contains any one of vulcanizing agent, carbon, calcium carbonate, titanium oxide, magnesium oxide and magnesium carbonate, becomes substantially equal to that of said water or living body and its acoustic attenuation coefficient becomes lower than that of silicon rubber.

2. An ultrasonic probe comprising:

an ultrasonic propagation medium provided directly or indirectly between said ultrasonic transducer means and said water or living body, said ultrasonic propagation medium being made of butadiene rubber, butadiene rubber which contains sulfur, vulcanization accelerator, zinc oxide and stearic acid or butadiene rubber which contains any one of vulcanizing agents, carbon, calcium carbonate, titanium oxide, magnesium oxide and magnesium carbonate, whereby its acoustic impedance becomes substantially equal to that of said water or living body and its acoustic attenuation coefficient becomes lower than that of silicon rubber; and an acoustic lens which is provided on a surface of said ultrasonic propagation medium opposite to the surface facing said ultrasonic transducer means so that said acoustic lens comes into contact with said water or living body.

3. An ultrasonic probe comprising:

first transducer means including an array of transducer elements for transmission of ultrasonic waves into a water or living body and for reception of echo waves returning from said water or living body;

second transducer means including a transducing member for transmission of ultrasonic waves into said water or living body and for reception of echo waves returning from said water or living body, said second transducer means being disposed such that the ultrasonic transmitting and receiving surface thereof is inclined to make an angle with respect to the ultrasonic transmitting and receiving surface of said transducer element array; and an ultrasonic propagation medium provided in front of at least said second transducer means and made of butadiene rubber, butadiene rubber which contains sulfur, vulcanization accelerator, zinc oxide and stearic acid, butadiene rubber which contains any one of vulcanizing agent, carbon, calcium carbonate, titanium oxide, magnesium oxide and magnesium carbonate, or butadiene rubber which is made of one of polymethyl pentene, polyethylene and thermoplastic elastomer, whereby the acoustic impedance of the ultrasonic propagation medium becomes substantially equal to that of said water or living body and its acoustic attenuation coefficient becomes lower than that of silicon rubber, wherein the contact surface of said ultrasonic propagation medium with said water or living body and the contact surface of said first transducer means with said water or living body are substantially on the same plane.

* * * * *